(12) United States Patent
Ramirez Corredores et al.

(10) Patent No.: US 9,447,000 B2
(45) Date of Patent: Sep. 20, 2016

(54) TAN UPGRADING OF BIO-OIL

(75) Inventors: Maria Magdalena Ramirez Corredores, Houston, TX (US); Xiaowei Tong, Houston, TX (US); Jennifer Sorrells, Houston, TX (US)

(73) Assignee: Inaeris Technologies, LLC, Pasadena, TX (US)

( * ) Notice: Subject to any disclaimer, the term of this patent is extended or adjusted under 35 U.S.C. 154(b) by 1144 days.

(21) Appl. No.: 13/443,566

(22) Filed: Apr. 10, 2012

(65) Prior Publication Data
US 2013/0267753 A1 Oct. 10, 2013

(51) Int. Cl.
*C07C 7/12* (2006.01)
*C10G 25/00* (2006.01)

(52) U.S. Cl.
CPC .............. *C07C 7/12* (2013.01); *C10G 25/003* (2013.01); *C10G 2300/203* (2013.01)

(58) Field of Classification Search
CPC .. C07C 7/12; C10G 2300/203; C10G 25/003
USPC ........................................................ 585/824
See application file for complete search history.

(56) References Cited

U.S. PATENT DOCUMENTS

| 4,762,529 A | * | 8/1988 | Schulz ..................... C10G 1/00 110/341 |
| 2006/0049167 A1 | | 3/2006 | Yang et al. |
| 2009/0294324 A1 | | 12/2009 | Brandvold et al. |
| 2010/0209371 A1 | | 8/2010 | Casado-Chaudanson et al. |
| 2011/0146141 A1 | | 6/2011 | Frey et al. |
| 2012/0017494 A1 | * | 1/2012 | Traynor ..................... C10L 1/02 44/388 |

OTHER PUBLICATIONS

Search Report and Written Opinion for corresponding PCT Patent Application No. PCT/US2013/035978, filed Apr. 10, 2013; Dated Jul. 23, 2013; 11 pages.

* cited by examiner

*Primary Examiner* — Latosha Hines
(74) *Attorney, Agent, or Firm* — Hovey Williams LLP

(57) ABSTRACT

A process to improve the processability of a bio-oil is provided. The disclosed process involves removing at least a portion of the carboxylic acids originally present in a bio-oil using a weak base anion exchange resin. Upon removing at least a portion of these carboxylic acids, the treated bio-oil contains a lower TAN value and is better suited for processing in existing refinery equipment.

30 Claims, 11 Drawing Sheets

TAN UPGRADING OF BIO-OIL

FIELD OF THE INVENTION

The present invention relates generally to bio-oils with enhanced processability and to processes for making such bio-oils.

BACKGROUND OF THE INVENTION

With the rising costs and environmental concerns associated with fossil fuels, renewable energy sources have become increasingly important. The development of renewable fuel sources provides a means for reducing the dependence on fossil fuels. Accordingly, many different areas of renewable fuel research are currently being explored and developed.

With its low cost and wide availability, biomass has increasingly been emphasized as an ideal feedstock in renewable fuel research. Consequently, many different conversion processes have been developed that use biomass as a feedstock to produce useful biofuels and specialty chemicals. One of the useful products that may be derived from biomass is a liquid product commonly referred to as "bio-oil."

Bio-oil may be processed into transportation fuels, hydrocarbon chemicals, and specialty chemicals. However, most bio-oils that are produced contain high amounts of organic acids such as carboxylic acids. Due to this high acid content, bio-oils can cause corrosion or fouling of conventional refinery equipment. Thus, a bio-oil's high acid content thereby inhibits its ability to be processed, stored, and refined in conventional refineries. In an attempt to remedy this problem, many bio-oils have been subjected to various upgrading processes in order to lower their acid content. Although these treated bio-oils may contain lower amounts of acid, such upgrading processes are not cost-effective and can decrease the overall bio-oil yield.

Accordingly, there is a need for an improved process for upgrading a bio-oil that effectively removes undesirable acidic components from the bio-oil, but does not negatively impact bio-oil yield at the same time.

SUMMARY OF INVENTION

In one embodiment of the present invention, a process for reducing the total acid number (TAN) in a feedstock is provided. The process comprises the steps of: contacting an initial feedstock comprising at least 60 weight percent of a bio-oil with an active ion exchange resin to thereby provide a treated feedstock and an acid-enriched ion exchange resin. In such a process, at least 70 weight percent of the initial feedstock is recovered as the treated feedstock. The treated feedstock has a TAN value that is at least 30 percent lower than the TAN value of the initial feedstock and a carboxylic acid content that is at least 50 percent lower than the carboxylic acid content of the initial feedstock.

In another embodiment of the present invention, a process for reducing the TAN in a feedstock is provided. The process comprises the steps of: (a) contacting an initial feedstock comprising a bio-oil with an active ion exchange resin to produce an acid-enriched ion exchange resin and a treated feedstock having a TAN value that is lower than the TAN value of the initial feedstock; (b) regenerating the acid-enriched ion exchange resin with at least one oxygenated organic solvent to thereby provide a regenerated ion exchange resin; and (c) repeating step (a) using the regenerated ion exchange resin as the active ion exchange resin, wherein the regenerated ion exchange resin is not subjected to swelling prior to step (c). The regenerating comprises: (i) contacting at least a portion of the acid-enriched ion exchange resin with the oxygenated organic solvent to thereby provide a solvent-enriched ion exchange resin and (ii) removing at least a portion of the oxygenated organic solvent from the solvent-enriched ion exchange resin to thereby provide the regenerated ion exchange resin.

BRIEF DESCRIPTION OF THE FIGURES

Embodiments of the present invention are described in detail below with reference to the attached figure, wherein.

DETAILED DESCRIPTION

The following detailed description of the invention references various embodiments. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

The present invention relates generally to the removal of undesirable acidic components from a bio-oil. It has been observed that bio-oil can contain high amounts of carboxylic acids that contribute to the corrosive nature of the bio-oil. The present invention focuses on the selective removal of at least a portion of these carboxylic acids in order to enhance the stability and processability of the bio-oil. In certain embodiments of the present invention, a process for removing at least a portion of these carboxylic acids is provided that comprises contacting the bio-oil with an ion exchange resin that selectively adsorbs at least a portion of the carboxylic acids in the bio-oil. The ion exchange resins can selectively remove at least a portion of the carboxylic acids from the bio-oil, while leaving most of the phenolic compounds in the bio-oil, which minimizes the overall impact on bio-oil yield. In such embodiments, it is the objective of the process to reduce the acidity and corrosiveness of the bio-oil, thus enhancing its ability to be transported to and refined in conventional refineries.

Figure 1:
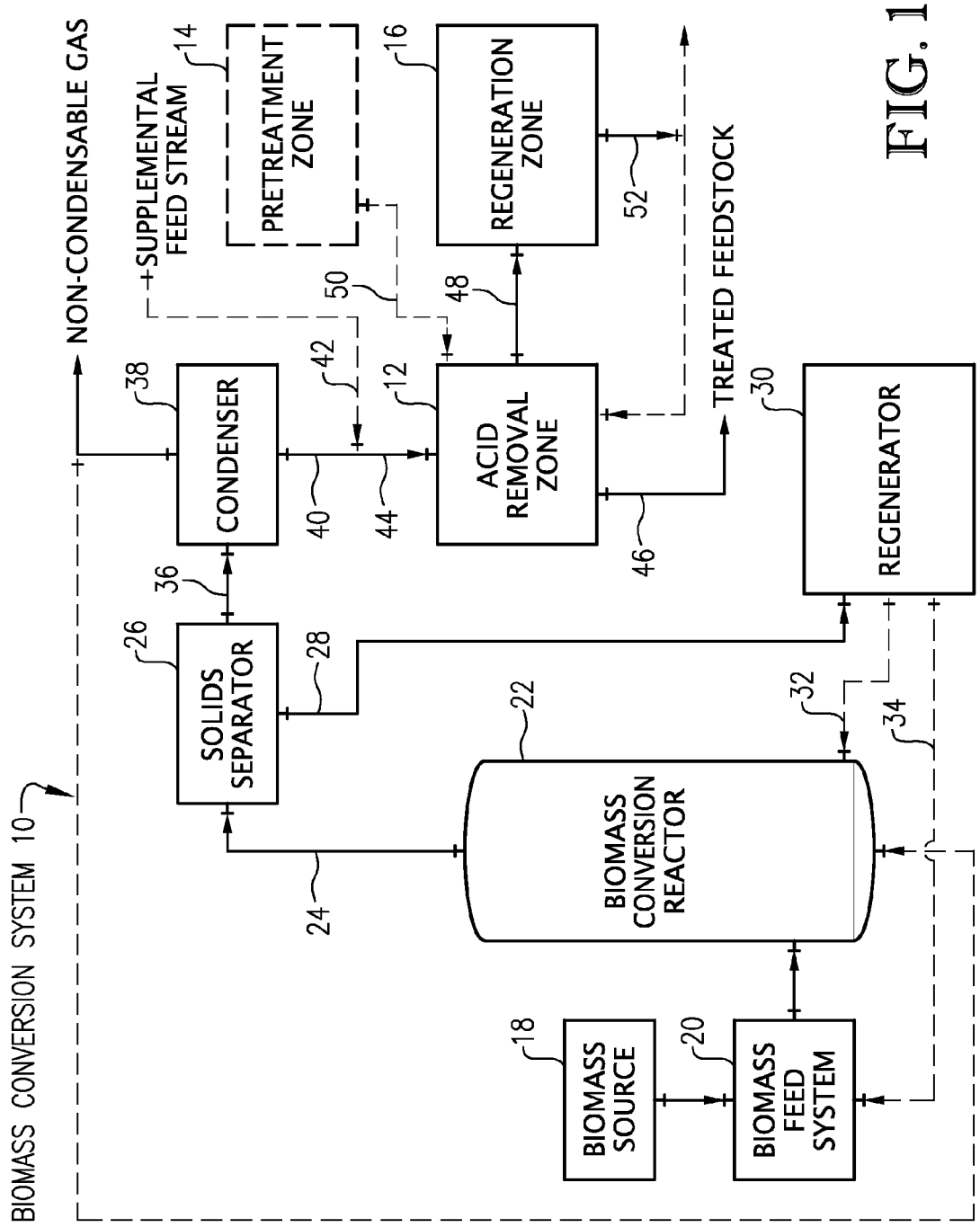
FIG. 1 is a schematic diagram of a biomass conversion system according to one embodiment of the present invention.

FIG. 1 depicts an exemplary embodiment of a biomass conversion system 10 suitable for producing a bio-oil having a reduced TAN. The biomass conversion system 10 of FIG. 1 can include an acid removal zone 12, an optional pretreatment zone 14, and a regeneration zone 16 for producing the bio-oil having a reduced TAN. It should be understood that the biomass conversion system 10 shown in FIG. 1 is just one example of a system within which the present invention can be embodied. The present invention may find application in a wide variety of other systems where it is desirable to efficiently and effectively produce bio-oil, upgrade bio-oil, and/or produce a number of useful products from the byproducts of biomass conversion. The exemplary biomass conversion system 10 illustrated in FIG. 1 will now be described in more detail.

The biomass conversion system 10 of FIG. 1 includes a biomass source 18 for supplying a biomass feedstock to the system. The biomass source 18 can be, for example, a hopper, storage bin, railcar, over-the-road trailer, or any other device that may hold or store biomass. The biomass supplied by the biomass source 18 can be in the form of solid particles. In one embodiment, the biomass particles can be fibrous biomass materials comprising cellulose. Examples of suitable cellulose-containing materials include algae, paper waste, and/or cotton linters. In another embodiment, the biomass particles can comprise a lignocellulosic material. Examples of suitable lignocellulosic materials include forestry waste such as wood particles, saw dust, pulping waste, and tree branches; agricultural waste such as corn stover, wheat straw, and bagasse; and/or energy crops such as eucalyptus, switch grass, and coppice.

As depicted in FIG. 1, the solid biomass particles from the biomass source 18 can be supplied to a biomass feed system 20. The biomass feed system 20 can be any system capable of feeding solid particulate biomass to a biomass conversion reactor 22. While in the biomass feed system 20, the biomass material may undergo a number of pretreatments to facilitate the subsequent conversion reactions. Such pretreatments may include drying, roasting, torrefaction, demineralization, steam explosion, mechanical agitation, grinding, milling, debarking, and any combination thereof.

In one embodiment, it may be desirable to combine the biomass with a catalyst in the biomass feed system 20 prior to introducing the biomass into the biomass conversion reactor 22. Alternatively, the catalyst may be introduced directly into the biomass conversion reactor 22. The catalyst may be fresh and/or regenerated catalyst. The catalyst can be a heterogeneous cracking catalyst such as, for example, a solid acid, an amorphous silica-alumina, alumina phosphates, or a zeolite. Examples of suitable zeolites include ZSM-5, ZSM-11, ZSM-12, ZSM-18, ZSM-22, ZSM-23, zeolite-L, Mordenite, Beta, Ferrierite, zeolite-Y, or combinations thereof. Additionally or alternatively, the catalyst may comprise a super acid. Examples of suitable super acids include Nafion-H, sulfonated, phosphated, or fluorinated forms of zirconia, titania, alumina, silica-alumina, and/or clays. In another embodiment, the catalyst may comprise a solid base. Examples of suitable solid bases include metal oxides, metal hydroxides, and/or metal carbonates. In particular, the oxides, hydroxides, and carbonates of alkali metals, alkaline earth metals, transition metals, and/or rare earth metals are suitable. Other suitable solid bases include layered double hydroxides, mixed metal oxides, hydrotalcite, clays, and combinations thereof. In yet another embodiment, the catalyst can also comprise an alumina, such as alpha-alumina.

In certain embodiments, the catalyst can be an equilibrium catalyst (E-cat) from a fluid catalytic cracking (FCC) unit of an oil refinery. This term refers to catalyst material that has, on average, circulated in the FCC unit for a considerable length of time. The term is used to distinguish fresh catalyst, which has not been exposed to the environment of the FCC unit, and which has much greater catalytic activity than the E-cat. This spent catalyst is a waste product from oil refineries, and as such, is abundantly available at low cost.

It should be noted that solid biomass materials generally contain minerals. It is recognized that some of these minerals, such as potassium carbonate, can have catalytic activity in the conversion of the biomass material. Even though these minerals are typically present during the chemical conversion taking place in the biomass conversion reactor 22, they are not considered catalysts.

As shown in FIG. 1, the biomass feed system 20 introduces the biomass feedstock into the biomass conversion reactor 22. In the biomass conversion reactor 22, biomass is subjected to a conversion reaction that produces a bio-oil. The reactor 22 can be any system or device capable of converting biomass to a bio-oil. The biomass conversion reactor 22 can be, for example, a fluidized bed reactor, a cyclone reactor, an ablative reactor, or a riser reactor. While in the biomass conversion reactor 22, the biomass feedstock can be subjected to thermochemical conversion or thermo-catalytic conversion in order to produce a biomass-derived liquid.

"Thermochemical conversion" as used herein refers to a non-catalytic conversion process such as, for example, fast pyrolysis, alkylation, isomerization, decarboxylation, or decarbonylation. In certain embodiments, the thermochemical conversion refers to fast pyrolysis processes, which convert all or part of the biomass to bio-oil by heating the biomass in an oxygen-poor or oxygen-free atmosphere. Fast pyrolysis utilizes much shorter residence times than conventional pyrolysis. For example, the residence times of fast pyrolysis can be less than 10, 5, 2, or 1 seconds. Additionally, fast pyrolysis can occur at temperatures of at least 200° C., 300° C., 400° C., or 500° C. and/or not more than 1,000° C., 800° C., 700° C., or 600° C. As used above, the term "oxygen-poor" refers to an atmosphere containing less oxygen than ambient air. In general, the amount of oxygen should be such as to avoid combustion of the biomass material, or vaporized and gaseous products emanating from the biomass material, at the pyrolysis temperature. Preferably, the atmosphere is essentially oxygen-free such that it contains less than about 1 weight percent oxygen. As used herein, "oxygen-free" refers to an atmosphere that is substantially free of molecular oxygen.

"Thermo-catalytic conversion" as used herein refers to a catalytic conversion process, wherein a catalyst is used to help facilitate cracking, alkylation, isomerization, decarboxylation, and/or decarbonylation of the biomass. In certain embodiments, the thermo-catalytic process occurs under fast pyrolysis conditions. Accordingly, in a biomass thermo-catalytic conversion process, a catalyst is used in the reactor 22 to facilitate the conversion of the biomass to bio-oil. As previously discussed, the catalyst can be pre-mixed with the biomass before introduction into the reactor 22 or it can be introduced into the reactor 22 separately.

In one embodiment, the biomass conversion reactor 22 can be a riser reactor with the conversion reaction being biomass thermo-catalytic conversion. As discussed above, the biomass thermo-catalytic conversion should occur in an oxygen-poor or, preferably, oxygen-free atmosphere. In another embodiment, biomass thermo-catalytic conversion is carried out in the presence of an inert gas, such as nitrogen, carbon dioxide, and/or steam. Alternatively, the biomass thermo-catalytic conversion can be carried out in the presence of a reducing gas, such as hydrogen, carbon monoxide, non-condensable gases recycled from the biomass conversion process, or combinations thereof.

Referring again to FIG. 1, the conversion effluent 24 exiting the biomass conversion reactor 22 generally comprises gas, vapors, and solids. As used herein, the vapors produced during the conversion reaction may interchangeably be referred to as "bio-oil," which is the common name for the vapors when condensed into their liquid state. In the case of biomass thermo-catalytic conversion, the solids in the conversion effluent 24 generally comprise particles of char, ash, unconverted portions of biomass, and/or spent catalyst. Because such solids, such as the unconverted biomass and spent catalyst, can contribute to the tendency of the bio-oil to form ash, it is particularly desirable to remove the solids so that the bio-oil is essentially solids-free. In one embodiment, the bio-oil has an ash content (i.e., solids content) of less than about 3000 ppmw, 2000 ppmw, or 1000 ppmw.

As depicted in FIG. 1, the conversion effluent 24 from the biomass conversion reactor 22 can be introduced into a solids separator 26. The solids separator 26 can be any conventional device capable of separating solids from gas and vapors such as, for example, a cyclone separator, a gas filter, or combinations thereof. The solids separator 26 removes a substantial portion of the solids (e.g., spent catalysts, char, and/or heat carrier solids) from the conversion effluent 24. The solid particles 28 recovered in the solids separator 26 can be introduced into a regenerator 30 for regeneration, typically by combustion. After regeneration, at least a portion of the hot regenerated solids can be introduced directly into the biomass conversion reactor 22 via line 32. Alternatively or additionally, at least a portion of the hot regenerated solids can be directed via line 34 to the biomass feed system 20 for combination with the biomass feedstock prior to introduction into the biomass conversion reactor 22.

The substantially solids-free stream 36 exiting the solids separator 26 can then be introduced into a condenser 38. Within the condenser 38, the vapors are condensed or partially condensed into a bio-oil stream 40 and separated from the non-condensable gases. In certain embodiments, the separated and condensed bio-oil has a total acid number (TAN) of at least 1, 3, 5, or 10 mg KOH/g and/or not more than 200, 150, 100, or 60 mg KOH/g. The TAN is defined as the number of milligrams of KOH necessary to neutralize the acidity of one gram of bio-oil and is measured according to ASTM D-664. In another embodiment, the separated and condensed bio-oil has an organic oxygen content of not more than 50, 35, 30, 25, 20, 15, or 10 weight percent. In yet another embodiment, the separated and condensed bio-oil has a water content of not more than 25, 20, 15, or 10 weight percent.

In certain embodiments, the separated and condensed bio-oil has a phenolic compounds content of at least 1, 2, 4, or 8 weight percent and/or not more than 60, 50, 40, or 35 weight percent. In another embodiment, the separated and condensed bio-oil has a cycloparaffins content of not more than 6, 4, 2, or 1 weight percent. In yet another embodiment, the separated and condensed bio-oil has a furanics content of at least 2, 4, or 6 weight percent.

As shown in FIG. 1, the separated non-condensable gases are removed from the condenser 38 as a non-condensable gas stream. The non-condensable gases removed from the condenser 38 may be, optionally, recycled to the biomass conversion reactor 22 for use as a lift gas.

Subsequent to exiting the condenser 38, the bio-oil stream 40 can be combined with an optional supplemental feed stream 42 to produce an initial feedstock 44. The supplemental feed stream 42 can comprise any refinery feedstock that can be readily combined with the bio-oil stream 40 such as, for example, petroleum-derived feedstocks, hydrocarbon-based feedstocks, biomass-derived feedstocks, pyrolysis oils, bio-oils, or mixtures thereof. In certain embodiments, the initial feedstock 44 comprises at least 60, 70, 80, 90, 95, or 98 weight percent of bio-oil.

Turning again to FIG. 1, the initial feedstock 44 can be introduced into an acid removal zone 12. In the acid removal zone 12, the initial feedstock 44 is contacted with an ion exchange resin to remove at least a portion of the acidic components from the initial feedstock 44 to thereby produce a treated feedstock 46 and an acid-enriched ion exchange resin 48. These acidic components can include, for example, carboxylic acids and their residues. The term "acid-enriched," as used herein, denotes that the ion exchange resin comprises a higher amount of acidic components when compared to its acid contents prior to contact with the initial feedstock 44. The acid-enriched ion exchange resin can comprise one or more acids and their residues that are derived from at least portion of the acidic components originally found in the bio-oil. In certain embodiments, the ratio of the initial feedstock 44 to the ion exchange resin that is contacted in the acid removal zone 12 is at least 5:1, 10:1, or 20:1 and/or not more than 200:1, 150:1, 100:1, or 50:1 by volume. The acid removal zone 12 can comprise any apparatus, container, or reactor that is capable of facilitating the contact between the initial feedstock 44 and the ion exchange resin such as, for example, a column.

In certain embodiments, the contacting between the initial feedstock 44 and the ion exchange resin in the acid removal zone 12 comprises: (a) swelling the ion exchange resin with at least a portion of the initial feedstock 44 and/or an oxygenated swelling solvent to thereby provide a swollen ion exchange resin, and (b) removing one or more acids from at least a portion of the initial feedstock 44 using the swollen ion exchange resin to thereby provide the treated feedstock 46 and the acid-enriched ion exchange resin 48. The oxygenated swelling solvent can comprise, for example, aliphatic alcohols, aliphatic ketones (e.g., acetone and MIBK), aliphatic ethers, and/or cyclic ethers (e.g., tetrahydrofuran). After removing at least a portion of its acidic components, the treated feedstock 46 can be separated from the acid-enriched ion exchange resin 48 by filtration, centrifugation, and/or decanting.

Subsequent to leaving the acid removal zone 12, the treated feedstock 46 has a lower acid content relative to the initial feedstock 44. In one embodiment, the treated feedstock has a TAN value that is at least 30, 40, 50, 65, 80, or 95 percent lower than the TAN value of the initial feedstock. In another embodiment, the treated feedstock has a carboxylic acid content that is at least 50, 60, 75, 90, or 95 percent lower than the carboxylic acid content of the initial feedstock. In yet another embodiment, the treated feedstock has a TAN value that is not more than 15, 10, 8, 6, or 5 mg KOH/g. In still yet another embodiment, the amount of oxygenated compounds in the treated feedstock is at least 3, 5, 10, or 15 percent lower than the amount of oxygenated compounds in the initial feedstock.

In certain embodiments, it is desirable that most of the initial feedstock 44 be converted into the treated feedstock 46 in order to maintain the bio-oil yield. For example, at least 60, 70, 80, 90, or 95 weight percent of the initial feedstock can be recovered as the treated feedstock.

In certain embodiments, the ion exchange resin comprises an anion exchange resin. In one embodiment, the anion exchange resin comprises at least one amine functionality. For example, the anion exchange resin can be selected from the group consisting of aliphatic amines, aromatic amines, and mixtures thereof. In another embodiment, the anion exchange resin is a weak base anion exchange resin. In yet another embodiment, the anion exchange resin is selected from the group consisting of an ion exchange resin from the Dowex™ series (Dow Chemical, Midland, Much.), an ion exchange resin from the Xus series (Dow Chemical, Midland, Mich.), an ion exchange resin from the Amberlyst™ series (Rohm & Haas, Midland, Mich.), and mixtures thereof. In such an embodiment, the anion exchange resin can be, for example, Amberlyst A-21.

In certain embodiments, the ion exchange resin can selectively remove certain acidic components and their residues that are originally found in the bio-oil and initial feedstock 44. In such embodiments, the ion exchange can selectively remove at least a portion of the carboxylic acids and the residues thereof from the initial feedstock 44, while leaving other slightly acidic components in the initial feedstock 44. These other acidic components that may be left in the treated feedstock 46 can include, for example, phenolic compounds and furanics. In one embodiment, the treated feedstock has a phenolic compounds content that is not more than 25, 15, 10, 5, or 1 percent lower than the phenolic compounds content of the initial feedstock. In another embodiment, the treated feedstock has a furanics content that is not more than 25, 15, 10, 5, or 1 percent lower than the furanics content of the initial feedstock. In addition, the treated feedstock 46 can retain much of the cycloparaffins originally found in the initial feedstock 44. In yet another embodiment, the treated feedstock has a cycloparaffins content that is not more than 25, 15, 10, 5, or 1 percent lower than the cycloparaffins content of the initial feedstock. In still yet another embodiment, the treated feedstock has a water content that is not more than 20, 15, 10, 5, or 1 percent lower than the water content of the initial feedstock.

Prior to being introduced into the acid removal zone 12, the ion exchange resin can be subjected to pretreatment in a pretreatment zone 14. While in the pretreatment zone 14, an initial ion exchange resin can be pretreated to produce an active ion exchange resin 50, which can then be introduced into the acid removal zone 12. Prior to pretreatment, the initial ion exchange resin can comprise significant amounts of water, which can negatively impact the ability of the ion exchange resin to adsorb acidic components from the initial feedstock 44. Therefore, the initial ion exchange resin can be pretreated to remove at least a portion of this water. In one embodiment, the pretreatment removes at least 50, 75, 90, or 95 weight percent of the water in the initial ion exchange resin. As shown in FIG. 1, the pretreatment zone 14 can be a separate zone or reactor from the acid removal zone 12 and can comprise any apparatus, container, or reactor capable of facilitating the pretreatment of the initial ion exchange resin. In an embodiment not depicted in FIG. 1, the pretreatment zone 14 can comprise the same space and/or zone as the acid removal zone 12.

In certain embodiments, the pretreatment comprises (a) contacting the initial ion exchange resin with at least one polar liquid, and (b) removing at least a portion of the polar liquid from the initial ion exchange resin to produce the active ion exchange resin 50. The polar liquid can be added to the initial ion exchange resin at a ratio of at least 1:1, 2:1, or 3:1 and/or not more than 20:1, 15:1, or 10:1 by volume. Generally, the polar liquid can be removed from the initial ion exchange resin by drying the mixture at a temperature of not more than 90, 80, 70, or 60° C. As used herein, an "active" ion exchange resin refers to an ion exchange resin that has undergone pretreatment as described above. In one embodiment, the ion exchange resin utilized in the acid removal zone 12 is an active ion exchange resin.

The polar liquid useful in the pretreatment process can be any polar liquid that is capable of removing at least a portion of the water in the initial ion exchange resin. In one embodiment, the polar liquid can have a boiling point of not more than 90, 80, 70, or 60° C. so that it can be readily removed from the initial ion exchange resin via drying. In another embodiment, the polar liquid comprises an oxygenated organic solvent such as, for example, aliphatic alcohols, aliphatic ketones (e.g., acetone and MIBK), aliphatic ethers, and/or cyclic ethers (e.g., tetrahydrofuran). In a particular embodiment, the polar liquid comprises methanol.

As depicted in FIG. 1, at least a portion of the acid-enriched ion exchange resin 48 can be introduced into a regeneration zone 16 in order to regenerate the acid-enriched ion exchange resin 48. In one embodiment, the regeneration zone 16 is separate from the acid removal zone 12 and can comprise any apparatus, container, or reactor capable of facilitating the regeneration of the acid-enriched ion exchange resin. In an alternative embodiment not depicted in FIG. 1, the regeneration zone 16 can comprise the same space and/or zone as the acid removal zone 12.

While in the regeneration zone 16, at least a portion of the acid-enriched ion exchange resin 48 can be regenerated with at least one oxygenated organic solvent to provide a regenerated ion exchange resin 52. The regeneration process is intended to remove at least a portion of the bio-oil compounds retained by the ion exchange resin and restore at least part of its exchange capacity. In certain embodiments, the acid-enriched ion exchange resin 48 is regenerated by (a) contacting the acid-enriched ion exchange resin 48 with the oxygenated organic solvent to thereby provide a solvent-enriched ion exchange resin, and (b) removing at least a portion of the oxygenated organic solvent from the solvent-enriched ion exchange resin to thereby provide the regenerated ion exchange resin 52. The oxygenated organic solvent can comprise any solvent that is compatible with the ion exchange resin and capable of removing acidic components from the ion exchange resin. For example, the oxygenated organic solvent can comprise aliphatic alcohols, aliphatic ketones (e.g., acetone and MIBK), aliphatic ethers, and/or cyclic ethers (e.g., tetrahydrofuran). In one embodiment, the oxygenated organic solvent can be methanol.

In certain embodiments, the regeneration process removes at least a portion of the acidic components and residues thereof previously adsorbed by the acid-enriched ion exchange resin 48. For example, the regeneration process can remove at least 50, 60, 70, 80, or 95 weight percent of the acidic components and residues thereof from the acid-enriched ion exchange resin 48.

In certain embodiments, at least a portion of the regenerated ion exchange resin 52 can be recycled and sent to the acid removal zone 12 to be used as the ion exchange resin. In such embodiments, an ion exchange resin can be utilized in the acid removal stage multiple times by subsequently regenerating the acid-enriched ion exchange resin after each use in the acid removal zone 12. For example, the ion exchange resin can be subjected to the acid removal stage, regenerated, and recycled at least 4, 8, 16, or 32 times. When used as the ion exchange resin in the acid removal zone 12, the regenerated ion exchange resin 52 is capable of treating the initial feedstock 44 just as effectively as the ion exchange resin initially used as described above. Therefore, in certain embodiments where at least a portion of the regenerated ion exchange resin 52 is utilized in the acid removal zone 12 as the ion exchange resin, the regenerated ion exchange 52 resin can produce a treated feedstock containing the same properties and ranges as described above.

In certain embodiments, the regenerated ion exchange resin 52 does not require pretreatment before being recycled and utilized in the acid removal zone 12. In one embodiment, the regenerated ion exchange resin 52 is not subjected to swelling or any other form of pretreatment prior to contacting the initial feedstock 44 in the acid removal zone 12.

EXAMPLES

This invention can be further illustrated by the following examples of preferred embodiments thereof, although it will be understood that these examples are included merely for purposes of illustration and are not intended to limit the scope of the invention unless otherwise specifically indicated.

Example 1

In this example, the capabilities of certain ion exchange resins in selectively removing carboxylic acids from bio-oil were assessed. In this particular example, the tested resins were Amberlyst A-21 and Dow XUS. The Amberlyst A-21 resin contains aliphatic amines and has a pKa of about 10, while the Dow XUS resin contains aromatic amines and has a pKa of about 5.

The resins were placed in a fixed bed column and were pretreated by swelling them with methanol. Swelling was carried out by rinsing the resins with at least three volumes of methanol (3:1 MeOH:resin volume ratio) for 20 minutes. The swelled resins were then dried in an oven overnight at 60° C.

The bio-oil was then treated with the pretreated resins by flowing the bio-oil through the column at a 1:4 bio-oil to resin volume ratio. Samples of the treated bio-oil were collected and evaluated for TAN and water content. The TAN of the bio-oil was measured by using ASTM method D664 and the water content was measured using Karl Fischer titration. In addition, the effect of contact time between the bio-oil and the resins on TAN values was also assessed. The results of this example are depicted in TABLE 1 below.

TABLE 1

| Contact time, hrs | Amberlyst A-21 0 | Dow XUS 1 | Amberlyst A-21 | Dow XUS 12 |
|---|---|---|---|---|
| Carbon, wt % | 77.06 | 74.85 | 78.04 | 77.37 | 76.5 |
| Hydrogen, wt % | 7.32 | 7.54 | 7.75 | 7.4 | 7.54 |
| Nitrogen, wt % | 0.07 | 0.18 | <0.05 | 0.14 | 0.24 |
| Oxygen, wt % | 14.84 | 13.95 | 12.99 | 13.96 | 13.71 |
| Water, wt % | 3.02 | 4.67 | 2.60 | 3.4 | 3.13 |
| TAN, mg KOH/g | 21.95 | 8.01 | 21.06 | 9.43 | 15.00 |

As shown above, Amberlyst A-21 was observed to cause a more significant decrease in the TAN value relative to Dow XUS. In addition, Amberlyst A-21 was capable of reducing the TAN value in less contact time relative to Dow XUS.

Example 2

In this example, the effect of drying the resin and the use of the bio-oil as the swelling solvent was investigated. Initially, 5 g of Amberlyst A-21 resin was contacted with 20 g of methanol and dried at ~60° C. for 16 hours. Subsequent to drying the resin, three doses of bio-oil, with each dose containing about 5 g of bio-oil, were subsequently contacted one at a time with the resin order to swell the resin. After swelling the resin with the three doses of bio-oil, the swollen resin was then contacted with an additional 33 subsequent doses of bio-oil at a liquid hourly space velocity ("LHSV") of about 0.5 to 2 (v/v) $min^{-1}$, with each dose containing 5 g of bio-oil, in order to treat each bio-oil dose. The TAN value, water content, and amount of recovered bio-oil was measured in each of the treated bio-oil doses.

Figure 2:
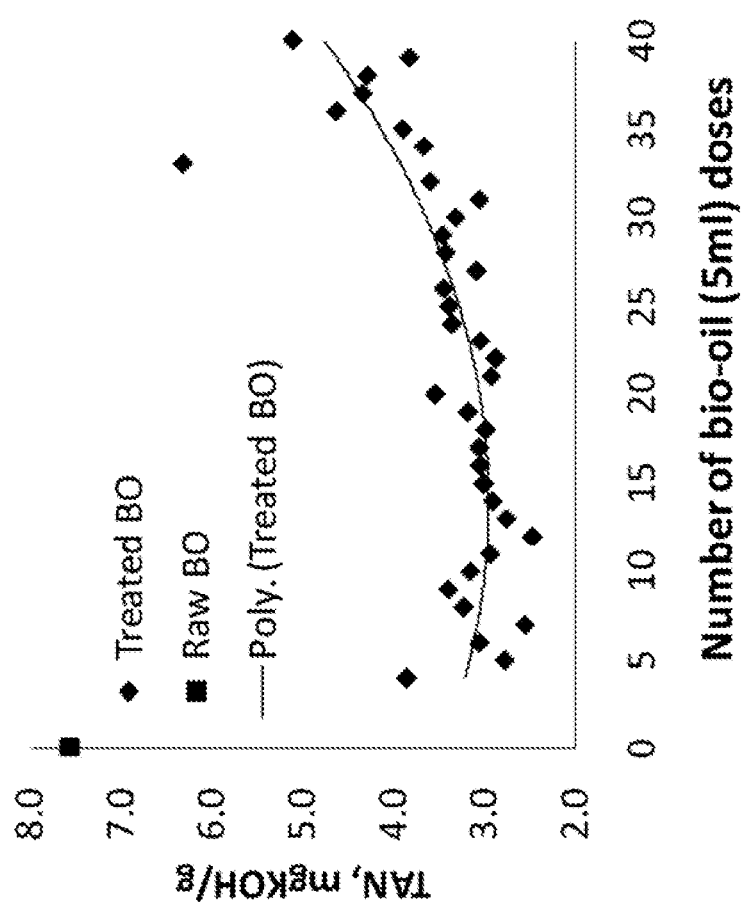
FIG. 2 is a graph depicting the TAN values of subsequent bio-oil doses after treatment with an Amberlyst A-21 resin according to one embodiment of the present invention.
Figure 3:
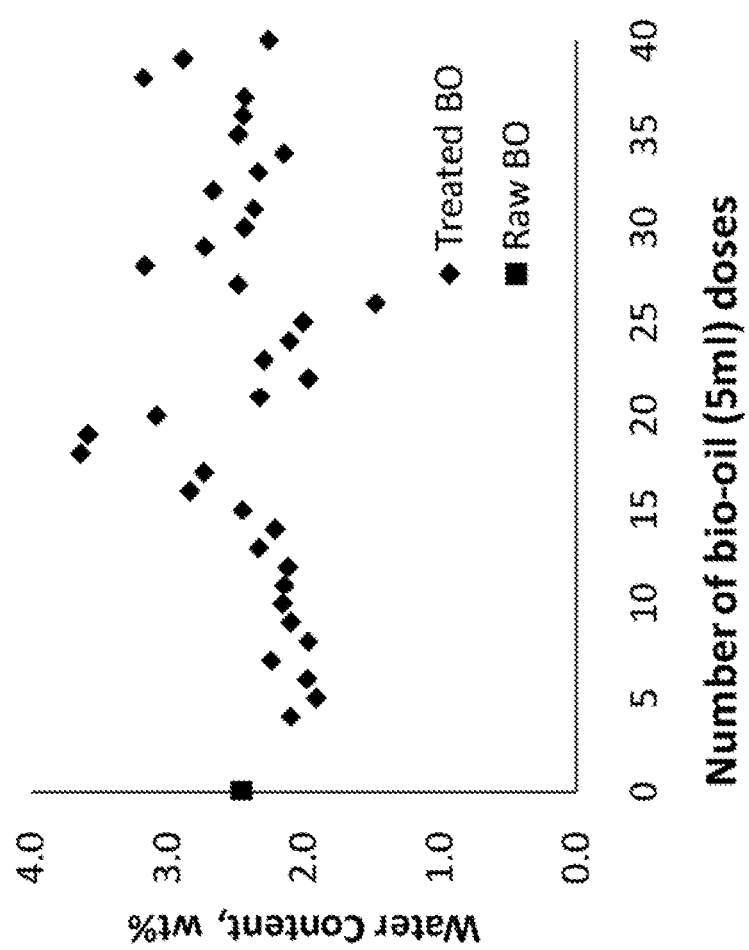
FIG. 3 is a graph depicting the water content of subsequent bio-oil doses after treatment with an Amberlyst A-21 resin according to one embodiment of the present invention.
Figure 4:
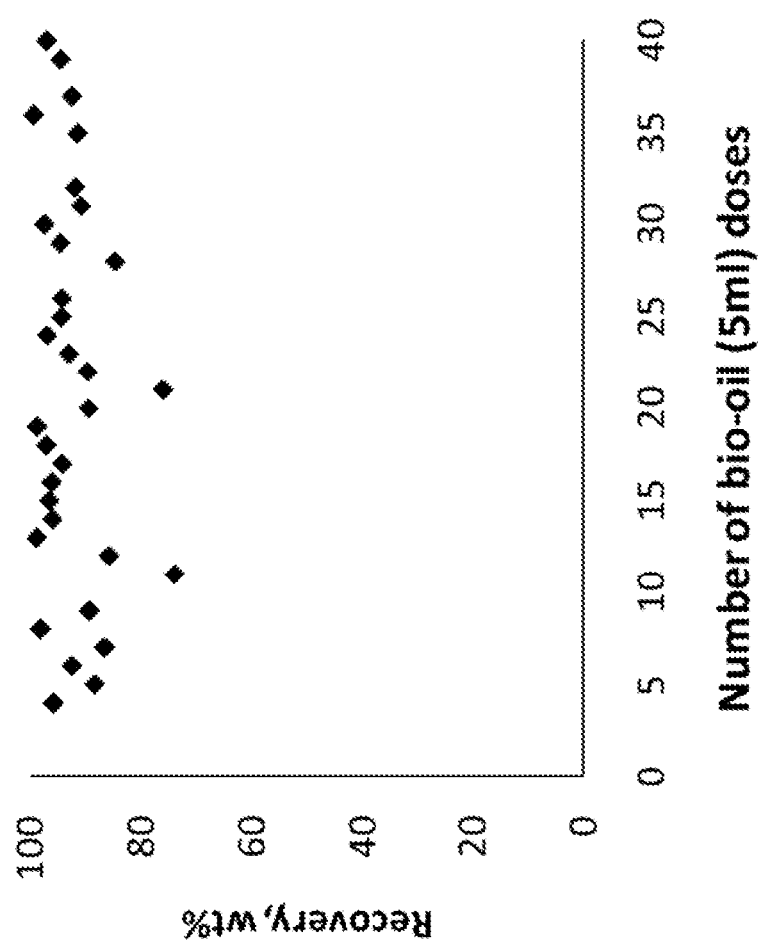
FIG. 4 is a graph depicting the amount of bio-oil recovered from the bio-oil doses subsequent to treatment with an Amberlyst A-21 resin according to one embodiment of the present invention.

As depicted in FIG. 2, the capability of the resin to remove acidic components from the bio-oil, thereby lowering its TAN, began to slowly deteriorate after about 20 doses of bio-oil. As shown in FIG. 3, the water content varied somewhat for each dose after being treated with the resin; however, this is most likely due to the moisture adsorption of the resin. The water content for each dose after treatment was around 2.5%. Finally, as shown in FIG. 4, the amount of bio-oil recovered from the bio-oil doses subsequent to treatment with the swollen resin remained consistently high in all of the bio-oil doses. Accordingly, these results indicate that drying might be an effective method of resin pretreatment and that the bio-oil itself might be used as swelling agent.

Example 3

In this example, the effect of regeneration on the resin was investigated. The Amberlyst A-21 resin of Example 2 was regenerated using 8 subsequent rinses of methanol, with each rinse containing 5 g of methanol. The regeneration was intended to remove any bio-oil compounds retained by the resin and restore the resin's exchange capacity. After rinsing, each methanol rinsing dose was evaluated for water content and TAN value.

Figure 5:
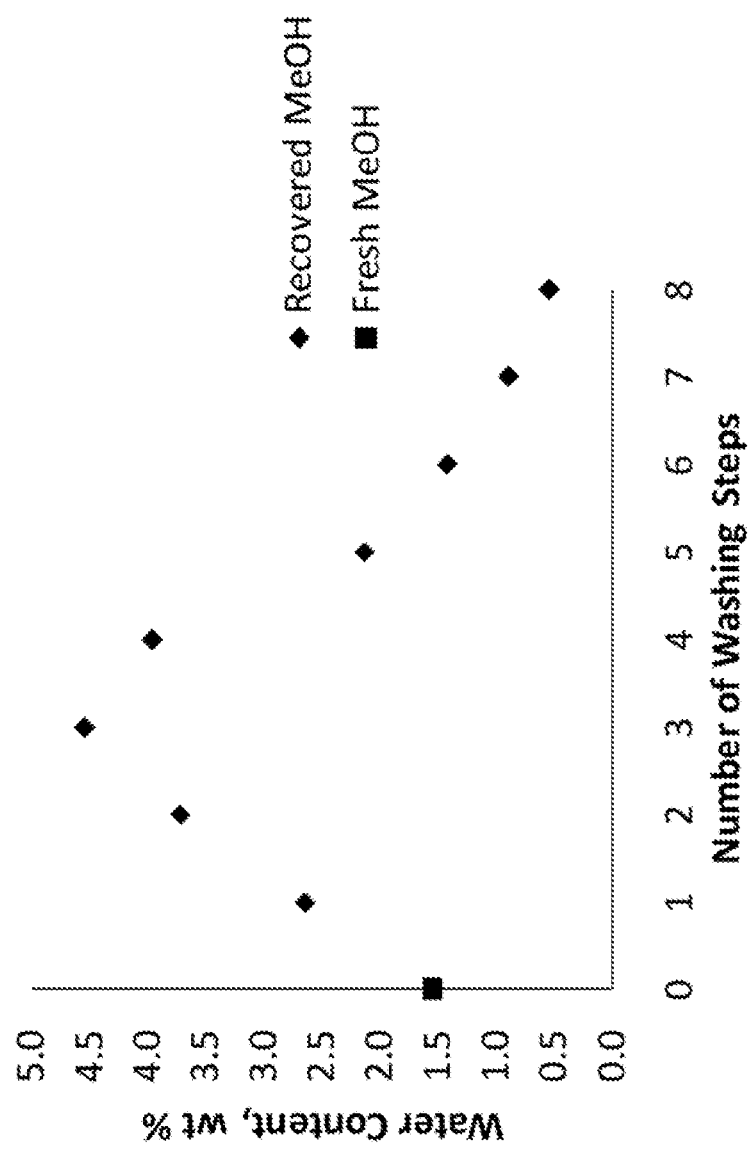
FIG. 5 is a graph depicting the water content of the methanol rinses subsequent to rinsing the Amberlyst A-21 resin according to one embodiment of the present invention.
Figure 6:
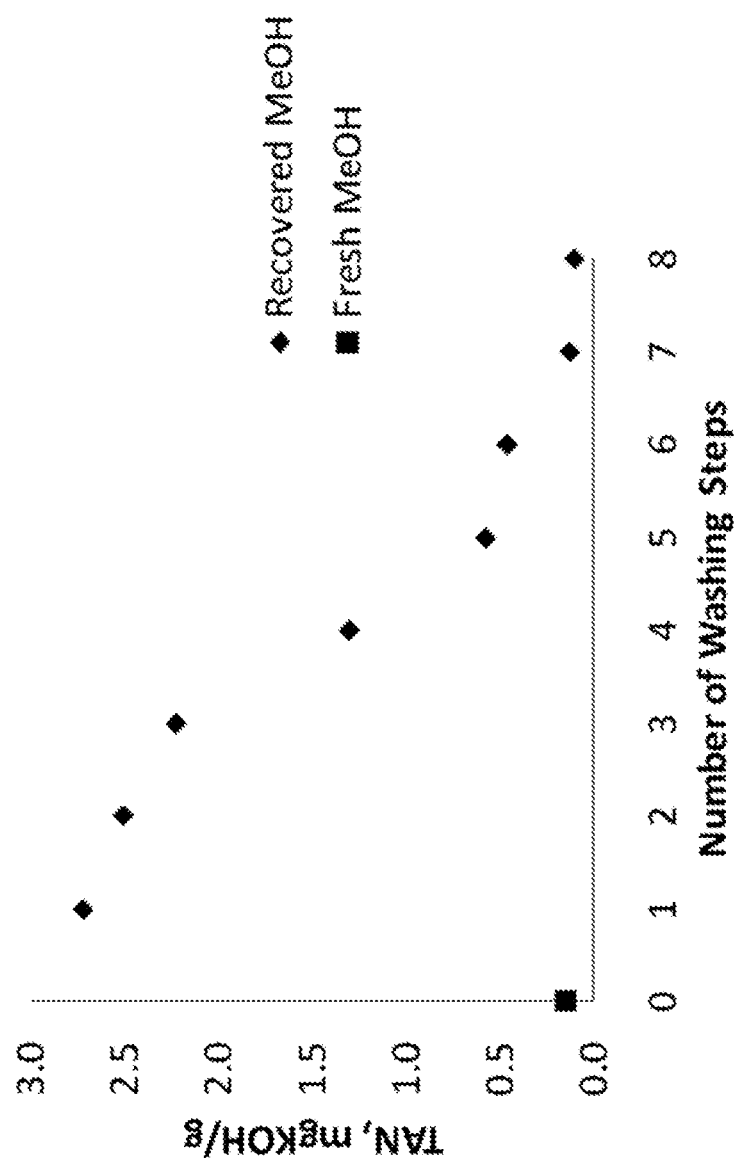
FIG. 6 is a graph depicting the TAN values of the methanol rinses subsequent to rinsing the Amberlyst A-21 resin according to one embodiment of the present invention.
Figure 7:
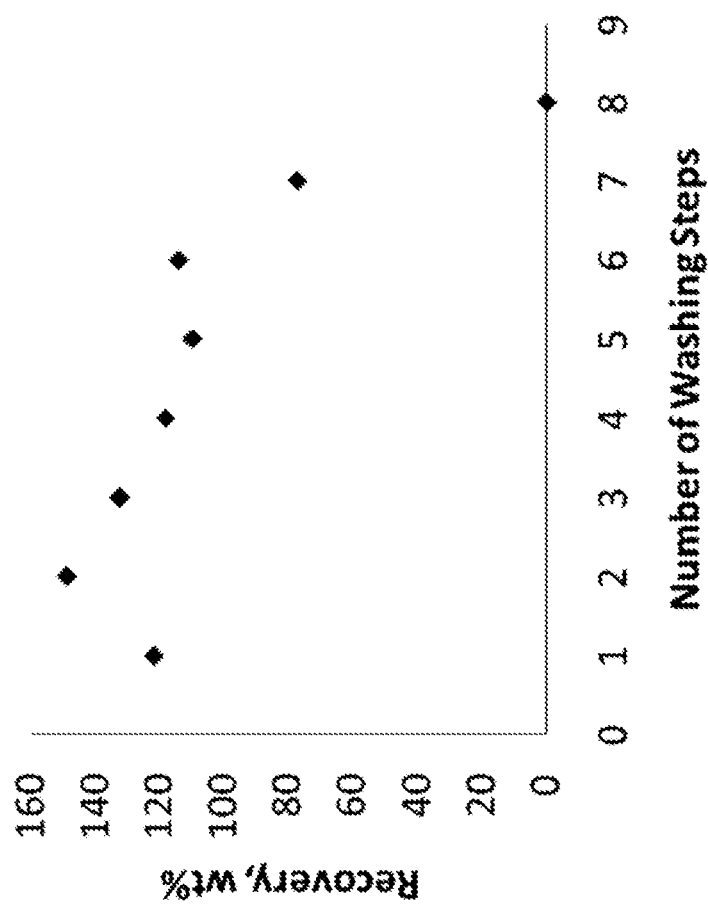
FIG. 7 is a graph depicting the amount of recovered products from each of the methanol rinses used to regenerate the Amberlyst A-21 resin according to one embodiment of the present invention.

As shown in FIG. 5, an increasing amount of water came out of the resin in the first three methanol rinses and peaked at 4.5% after the third rinse. Subsequently, the water content after the third methanol rinse decreased steadily. This decrease indicated that there was very little water left in the resin to remove after the fifth rinse with methanol. In fact, it appears that the resin actually removed some of the water from the methanol in the seventh and eighth doses. In addition, about five rinses with methanol were sufficient to remove most of the acidic components from the resin. This was shown by monitoring the TAN values of the methanol rinses as shown in FIG. 6. The amount of acidic components removed from the resin subsequent to the fifth rinsing with methanol was low compared to the first five methanol rinses. Finally, as shown in FIG. 7, the first six methanol rinses recovered a greater volume of products from the resin when compared to the initial volume of the methanol rinse. This confirms that the methanol was removing components retained by the resin in these first six rinses. After the sixth methanol rinse, the resin began to retain some of the methanol, thereby swelling the resin. Subsequent to swelling, the swollen resin was subjected to drying at ~60° C. for 16 hours in order to completely regenerate the resin.

Example 4

Figure 8:
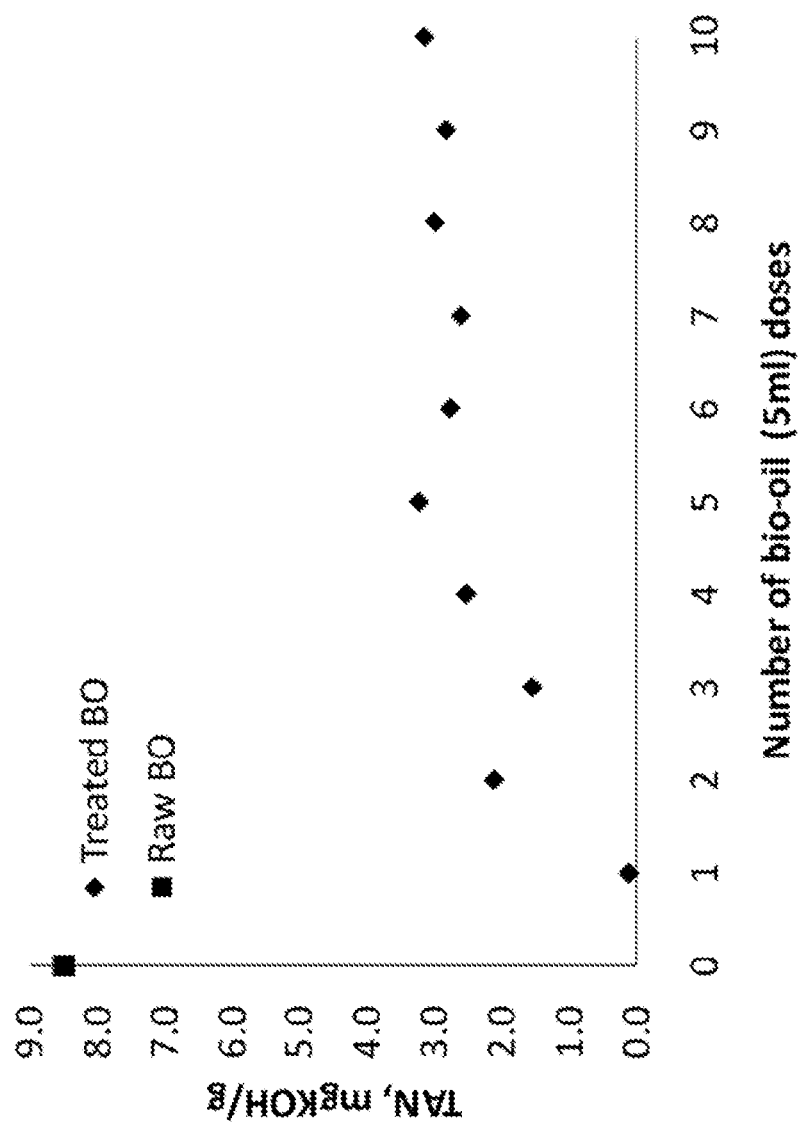
FIG. 8 is a graph depicting the TAN values of subsequent bio-oil doses after treatment with a regenerated Amberlyst A-21 resin according to one embodiment of the present invention.

In this example, the TAN-reducing performance of the regenerated Amberlyst A-21 resin from Example 3 was evaluated. The regenerated resin was utilized for treating and removing acidic components from bio-oil. More specifically, ten subsequent doses of bio-oil, with each dose containing 5 g of bio-oil, were brought into contact with the regenerated resin at a LHSV of about 1 (v/v) mid$^{-1}$. The first three doses of bio-oil functioned as the swelling solvents, thereby swelling the regenerated resin. As shown in FIG. 8, the regenerated resin was able to consistently reduce the TAN values of the bio-oil. It should also be noted that the first three doses of bio-oil contained a lower TAN value relative to the subsequent doses. While the resin did likely remove acidic components from the bio-oil in this case, it is likely that the recovered bio-oil in these doses was slightly diluted with methanol since the regenerated resin was dried subsequent to regeneration.

Example 5

Figure 9:
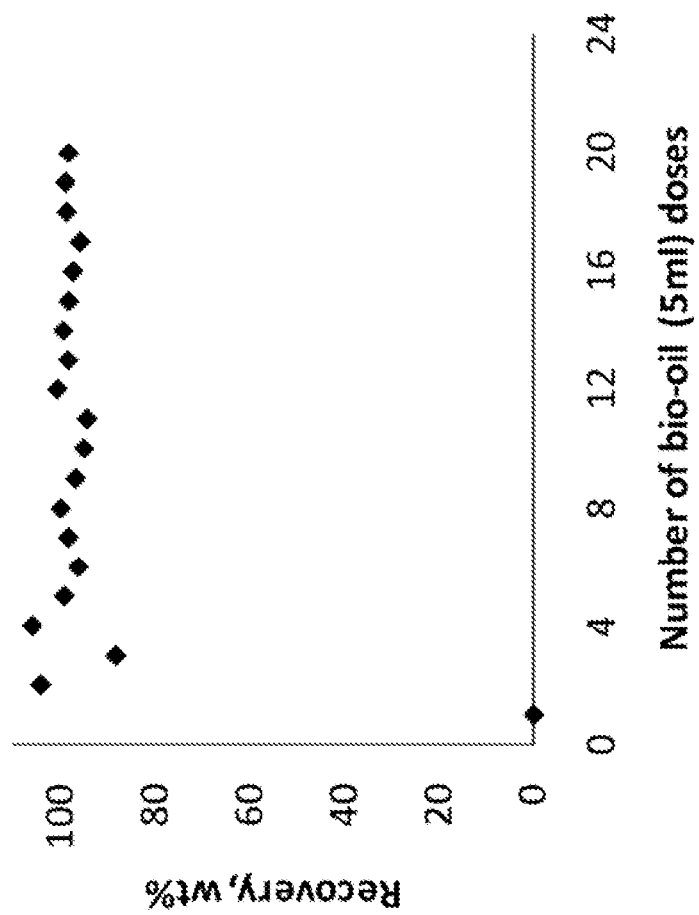
FIG. 9 is a graph depicting the amount of bio-oil recovered from the bio-oil doses subsequent to treatment with a regenerated Amberlyst A-21 resin according to one embodiment of the present invention.
Figure 10:
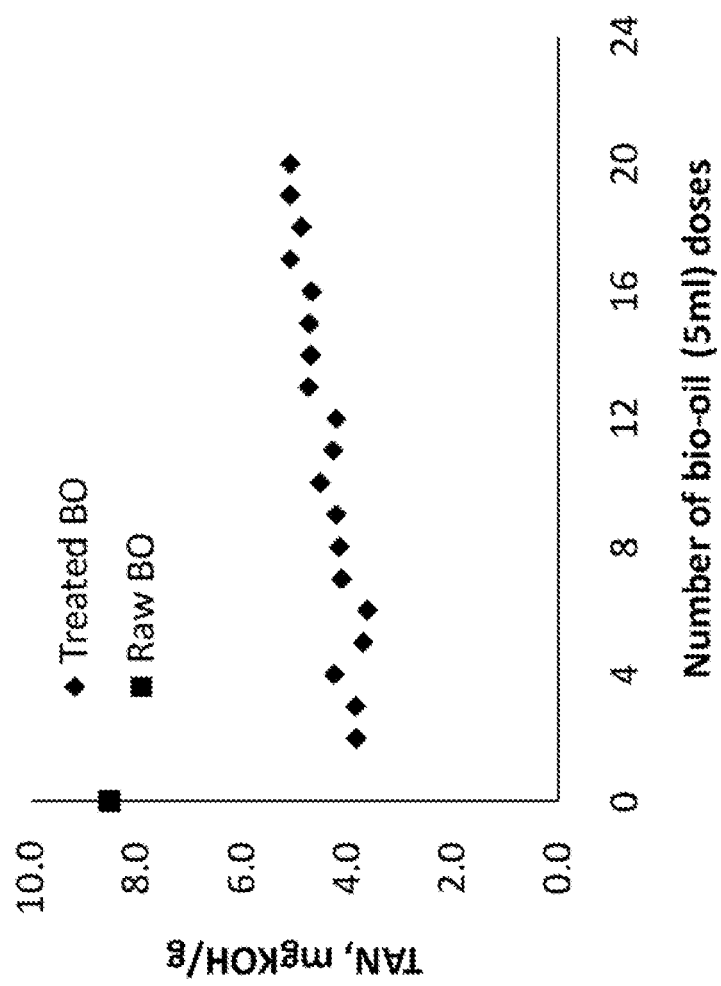
FIG. 10 is a graph depicting the TAN values of subsequent bio-oil doses after treatment with a regenerated Amberlyst A-21 resin according to one embodiment of the present invention.
Figure 11:
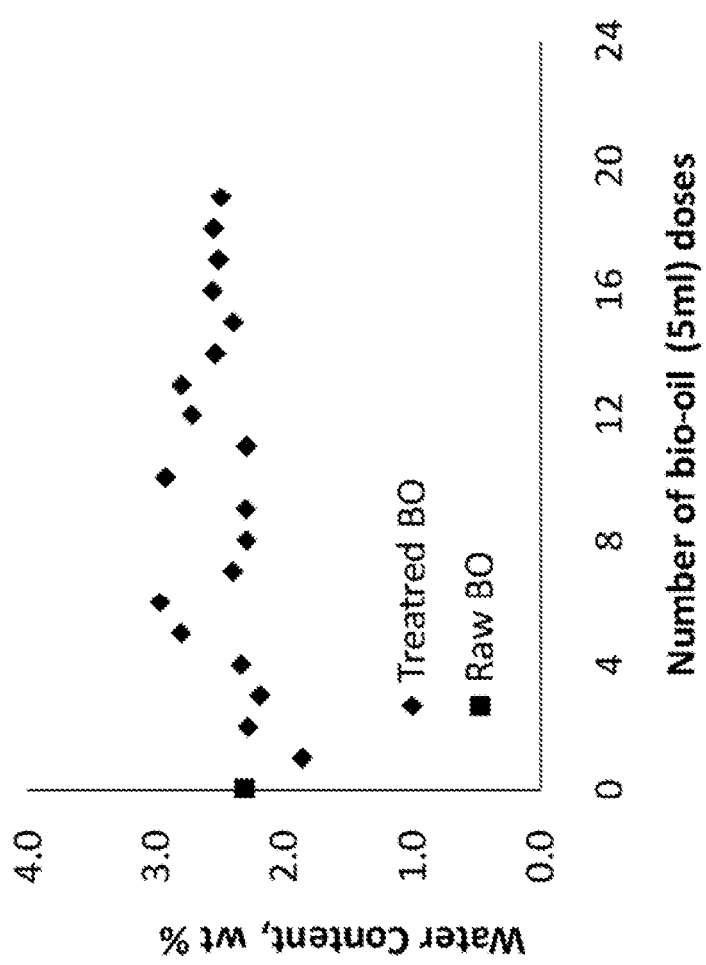
FIG. 11 is a graph depicting the water content of subsequent bio-oil doses after treatment with a regenerated Amberlyst A-21 resin according to one embodiment of the present invention.

In this example, the spent resin from Example 4 was regenerated and subsequently utilized to remove acidic components from bio-oil. In particular, the spent resin from Example 4 was regenerated with three separate methanol rinses, with each rinse containing 5 g of methanol. Subsequent to regeneration, the regenerated resin was dried at 60° C. The dried regenerated resin was then utilized for treating and removing acidic components from bio-oil. More specifically, twenty subsequent doses of bio-oil, with each dose containing 5 g of bio-oil, were brought into contact one at a time with the dried regenerated resin at a LHSV of about 1 (v/v) min$^{-1}$. The entire first dose of bio-oil functioned as the swelling solvent, thereby swelling the dried regenerated resin. Thus, as shown in FIG. 9, no bio-oil was recovered from this first dose. However, subsequent to the first dose, the bio-oil recovery rate went up to be consistently around 98%. In addition, as shown in FIG. 10, the regenerated resin was capable of lowering the TAN of the bio-oil, subsequent to the first dose, by at least 40% after treatment. Finally, FIG. 11 shows that the water content of the treated bio-oil remained consistent in each dose after treatment.

The inventors hereby state their intent to rely on the Doctrine of Equivalents to determine and assess the reasonably fair scope of the present invention as it pertains to any apparatus not materially departing from but outside the literal scope of the invention as set forth in the following claims.

What is claimed is:

1. A process for reducing the TAN of a feedstock, said process comprising: contacting an initial feedstock comprising at least 60 weight percent of a bio-oil with an active ion exchange resin to thereby provide a treated feedstock and an acid-enriched ion exchange resin,
    wherein at least 70 weight percent of said initial feedstock is recovered as said treated feedstock,
    wherein said treated feedstock has a TAN value that is at least 30 percent lower than the TAN value of said initial feedstock,
    wherein said treated feedstock has a carboxylic acid content that is at least 50 percent lower than the carboxylic acid content of said initial feedstock,
    wherein said active ion exchange resin comprises an anion exchange resin.

2. The process of claim 1 wherein the ratio of said initial feedstock to said ion exchange resin is at least 5:1 by volume.

3. The process of claim 1 wherein said process further comprises pretreating an initial ion exchange resin to thereby form said active ion exchange resin.

4. The process of claim 3 wherein said initial ion exchange resin comprises water and said pretreating removes at least 50 weight percent of the water from said initial ion exchange resin.

5. The process of claim 3 wherein said pretreating comprises contacting said initial ion exchange resin with a polar liquid and removing at least a portion of said polar liquid from said initial ion exchange resin.

6. The process of claim 5 wherein said removing is carried out at a temperature of not more than 90° C., wherein said polar liquid has a boiling point of not more than 90° C.

7. The process of claim 5 wherein said polar liquid is added to said initial ion exchange resin at a ratio of at least 1:1 and not more than 20:1 by volume, wherein said polar liquid comprises an oxygenated organic solvent.

8. The process of claim 5 wherein said polar liquid comprises an aliphatic alcohol, an aliphatic ketone, an aliphatic ether, a cyclic ether, or combinations thereof.

9. The process of claim 5 wherein said polar liquid comprises methanol.

10. The process of claim 1 wherein said initial feedstock has a TAN value of at least 1 mg KOH/g and not more than 200 mg KOH/g, a water content of not more than 20 weight percent, and an organic oxygen content of not more than 50 weight percent.

11. The process of claim 1 wherein said treated feedstock has a TAN value that is at least 40 percent lower than the TAN value of said initial feedstock.

12. The process of claim 1 wherein said treated feedstock has a carboxylic acid content that is at least 60 percent lower than the carboxylic acid content of said initial feedstock.

13. The process of claim 1 wherein said anion exchange resin is a weak base anion exchange resin.

14. The process of claim 1 wherein said anion exchange resin is selected from the group consisting of aliphatic amines, aromatic amines, and mixtures thereof.

15. The process of claim 1 wherein said treated feedstock has a phenolic compounds content that is not more than 25 percent lower than the phenolic compounds content of said initial feedstock, wherein said initial feedstock has a phenolic compounds content of at least 1 weight percent and not more than 60 weight percent.

16. The process of claim 1 wherein the amount of oxygenated compounds in said treated feedstock is at least 3 percent lower than the amount of oxygenated compounds in said initial feedstock.

17. The process of claim 1 wherein said initial feedstock comprises at least 80 weight percent of said bio-oil.

18. The process of claim 1 wherein at least 90 weight percent of said initial feedstock is recovered as said treated feedstock.

19. The process of claim 1 wherein said treated feedstock has a cycloparaffins content that is not more than 25 percent lower than the cycloparaffins content of said initial feedstock.

20. The process of claim 1 wherein said treated feedstock has a furanics content that is not more than 25 percent lower than the furanics content of said initial feedstock.

21. The process of claim 1 wherein said treated feedstock has a water content that is not more than 20 percent lower than the water content of said initial feedstock.

22. A process for reducing the TAN of a feedstock, said process comprising:
  (a) contacting an initial feedstock comprising a bio-oil with an active ion exchange resin, wherein during at least a portion of said contacting of step (a), a treated feedstock and an acid-enriched ion exchange resin are produced, wherein said treated feedstock has a TAN value that is lower than the TAN value of said initial feedstock, wherein said active ion exchange resin comprises an anion exchange resin;
  (b) regenerating said acid-enriched ion exchange resin with at least one oxygenated organic solvent to thereby provide a regenerated ion exchange resin, wherein said regenerating comprises—
    (i) contacting said acid-enriched ion exchange resin with said oxygenated organic solvent to thereby provide a solvent-enriched ion exchange resin, and
    (ii) removing at least a portion of said oxygenated organic solvent from said solvent-enriched ion exchange resin to thereby provide said regenerated ion exchange resin; and
  (c) repeating step (a) using said regenerated ion exchange resin as said active ion exchange resin, wherein said regenerated ion exchange resin is not subjected to swelling prior to step (c).

23. The process of claim 22 wherein said contacting of step (a) includes:
  (i) swelling said active ion exchange resin with at least a portion of said initial feedstock or an oxygenated swelling solvent to thereby provide a swollen ion exchange resin, and
  (ii) removing one or more acids from said initial feedstock using said swollen ion exchange resin to thereby provide said treated feedstock and said acid-enriched ion exchange resin.

24. The process of claim 23 wherein said oxygenated swelling solvent comprises an aliphatic alcohol, an aliphatic ketone, an aliphatic ether, a cyclic ether, or combinations thereof.

25. The process of claim 22 wherein steps (a)-(c) are repeated at least 4 times.

26. The process of claim 22 wherein said acid-enriched ion exchange resin comprises one or more acidic components and residues thereof derived from said bio-oil.

27. The process of claim 26 wherein said regenerating removes at least 50 weight percent of said one or more acidic components and residues thereof from said acid-enriched ion exchange resin.

28. The process of claim 27 wherein said one or more acidic components and residues thereof comprise one or more carboxylic acids.

29. The process of claim 22 wherein, during step (c), at least 70 weight percent of said initial feedstock is recovered as said treated feedstock, wherein said treated feedstock has a TAN value that is at least 30 percent lower than the TAN value of said initial feedstock, wherein said treated feedstock has a carboxylic acid content that is at least 50 percent lower than the carboxylic acid content of said initial feedstock.

30. The process of claim 22 wherein, during step (c), at least 90 weight percent of said initial feedstock is recovered as said treated feedstock, wherein said treated feedstock has a TAN value that is at least 50 percent lower than the TAN value of said initial feedstock, wherein said treated feedstock has a phenolic compounds content that is not more than 25 percent lower than the phenolic compounds content of said initial feedstock.

* * * * *